United States Patent
Oshima et al.

(10) Patent No.: US 7,834,212 B2
(45) Date of Patent: Nov. 16, 2010

(54) POROUS SUBSTANCE AND PROCESS FOR PRODUCING THE SAME

(75) Inventors: Shinji Oshima, Yokohama (JP); Yoshihiro Kobori, Yokohama (JP)

(73) Assignee: Nippon Oil Corporation, Tokyo (JP)

( * ) Notice: Subject to any disclaimer, the term of this patent is extended or adjusted under 35 U.S.C. 154(b) by 360 days.

(21) Appl. No.: 11/951,609

(22) Filed: Dec. 6, 2007

(65) Prior Publication Data

US 2008/0095684 A1  Apr. 24, 2008

Related U.S. Application Data

(63) Continuation of application No. PCT/JP2006/311463, filed on Jun. 1, 2006.

(30) Foreign Application Priority Data

| Jun. 6, 2005 | (JP) | ............................ 2005-165770 |
| Sep. 14, 2005 | (JP) | ............................ 2005-266732 |

(51) Int. Cl.
- *C07F 5/02* (2006.01)
- *C01B 35/14* (2006.01)
- *C01B 21/087* (2006.01)
- *C01B 3/02* (2006.01)
- *B01J 20/26* (2006.01)

(52) U.S. Cl. ........................... 564/8; 423/284; 423/413; 423/648.1; 502/402; 521/128

(58) Field of Classification Search ............... 423/244.1, 423/284, 413, 648.1; 502/402; 521/128; 564/8

See application file for complete search history.

(56) References Cited

U.S. PATENT DOCUMENTS

| 2006/0008392 A1 | 1/2006 | Graham et al. |
| 2007/0039474 A1* | 2/2007 | Narula et al. ................. 96/108 |

FOREIGN PATENT DOCUMENTS

| EP | 1614955 A1 | 1/2006 |
| JP | 2005-067922 A | 3/2005 |
| JP | 2005-203188 | * 7/2005 |
| JP | 2005-203188 A | 7/2005 |
| JP | 2005-232222 A | 9/2005 |

OTHER PUBLICATIONS

Emeleus et al., "Advances in Inorganic Chemistry and Radiochemistry." (Eds.) Academic Press, vol. 16 (1974), p. 248.*

Kobayashi; Study of Introduction Scenario of Fuel Cell Vehicle; Quarterly IAE Review; 25:4, pp. 73-87 (2003).

(Continued)

*Primary Examiner*—Timothy C Vanoy
*Assistant Examiner*—Daniel Berns
(74) *Attorney, Agent, or Firm*—Panitch Schwarze Belisario & Nadel LLP

(57) ABSTRACT

A process is provided for producing a porous substance, which is lightweight, and has a highly developed pore structure and an excellent gas absorbability, by dehydrogenating a compound having two or more amine-borane adduct structures per molecule.

8 Claims, 1 Drawing Sheet

OTHER PUBLICATIONS

N. Kuriyama; The Trend of Hydrogen Storage Technology; Japan Society of Energy and Resources; 24:6, pp. 23-27 (2003).

Akiyama et al.; High Pressure Container-Hydrogen Storage Technology; Engine Technology; 5:3, pp. 43-47 (2003).

E. Akiba; Hydrogen Storage by Hydrogen Storage Materials; Engine Technology; 5:3, pp. 36-42 (2003).

A. Chambers et al.; Hydrogen Storage in Graphite Nanofibers; The Journal of Physical Chemistry B; 102:22, pp. 4253-4256 (1998).

Renzhi Ma et al.; Hydrogen Uptake in Boron Nitride Nanotubes at Room Temperature; Journal of the American Chemical Society; 124, pp. 7672-7673 (2002).

N. L. Rosi, et al.; Hydrogen Storage in Microporous Metal-Organic Frameworks; Science; 300:5622, pp. 1127-1129 (2003).

* cited by examiner

POROUS SUBSTANCE AND PROCESS FOR PRODUCING THE SAME

CROSS-REFERENCE TO RELATED APPLICATIONS

This application is a continuation of International Application No. PCT/JP2006/311463, filed Jun. 1, 2006, which was published in the Japanese language on Dec. 14, 2006, under International Publication No. WO 2006/132292, the disclosure of which is incorporated herein by reference.

BACKGROUND OF THE INVENTION

The present invention relates to a porous substance useful as gas-absorbing materials or catalyst supports, and a process for producing such a porous substance.

Porous substances including metal oxides such as zeolite, silica and alumina and activated carbon are industrially valuable as catalysts, catalyst supports, adsorbents or the like. In particular, it has been known that substances with highly developed pores are high in reactivity and absorption selectivity and in dispersibility of catalytic activated species. In view of this, carbon nanotubes, carbon nanohorns, and boron nitride nanotubes have been drawing an attention. However, since the large-scale production of these substances are difficult, there is a limit in industrial views to produce these substances at a low production cost.

Further, important future roles of porous substances are applications thereof to storage and transport of hydrogen or methane. In particular, storage and transport of hydrogen are technically difficult but are significantly important.

Hydrogen has been used in various industrial fields such as chemical industries and recently expected to be an energy for the future. As the result, studies mainly regarding fuel cells have been progressed. However, since hydrogen gas is large in volume per calorie and requires a large amount of energy for liquefaction, there is a problem that it is difficult to store or transport hydrogen gas as it is (see, for example, non-patent document 1 below). Therefore, a method has been demanded in which hydrogen is efficiently transported and stored for the case where a fuel cell is used in transportation devices such as fuel cell-powered vehicles or as decentralized electric sources.

As such a method, there has been proposed a method wherein hydrogen is stored and transported in the form of liquid hydrogen. However, there are problems that liquid hydrogen is difficult in handling because its liquefying temperature is −253° C. which is extremely low and the energy required for liquefaction of hydrogen is enormous, leading to a low overall energy efficiency (see, for example, non-patent document 2 below).

On the other hand, a method has been put in practical use, wherein hydrogen is transported and used as a high pressure gas. However, this method has problems that such a high pressure gas is dangerous in handling and it is difficult to compress hydrogen gas to a small volume even with an extremely high pressure of 35 MPa because the resulting volume is still large (see, for example, non-patent document 2 below).

Absorption of hydrogen to a hydrogen-absorbing alloy is also an effective method. However, the alloy can absorb hydrogen in an amount of usually on the order of 3 percent, which is insufficient to be used in transportation devices, and makes the weight thereof too heavy. Further, the alloy has disadvantages that it requires lots of energy to discharge hydrogen, resulting in poor energy efficiency and also makes the system more complicated (see, for example, non-patent document 4 below).

Alternatively, it has been considered to use a hydrogen-absorbing material as a method for compacting hydrogen gas for transportation purposes. This method has features that it is capable of discharging hydrogen at ambient temperatures and thus simplifying the system and is high in energy efficiency because of no necessity of heat to discharge hydrogen. Therefore, the development of materials for use in this method have been rigorously carried out. It has been reported that materials such as carbon nanotubes and carbon nanofibers exhibit high absorbability (see, for example, non-patent document 5 below). However, reproducibility of these materials are in question. Under the current situations, it is hardly say that the development of a hydrogen-absorbing material with sufficient reproducibility and high absorbability has been accomplished.

Therefore, the development of a material with high absorbability has been demanded, and a consideration has been given to the use of materials with pores, the size of which is in the same level as hydrogen, as such high absorbability materials. Examples of the materials include the above-mentioned carbon nanotubes and carbon nanofibers. In addition, the use of various materials mainly such as carbonaceous material have been attempted. Further, there are some reports introducing boron nitride nanotubes or porous complexes as materials other than carbons (see, for example, non-patent documents 6 and 7 below). However, there are some materials exhibiting high absorbability, in these reports, but the matter of fact is that the data therein are not reliable.

(1) Non-patent document 1: an article written by Kobayashi in "Kihou Energy Sogokogaku" vol. 25, No. 4, pages 73-87 published by The Institute of Applied Energy in 2003

(2) Non-patent document 2: an article written by Kuriyama in "Energy and Resources" vol. 24, No. 6, pages 23-27 published by Japan Society of Energy and Resources in 2003

(3) Non-patent document 3: an article written by Akiyama et al. in "Engine Technology" vol. 5, No. 3, pages 43-47 co-edited by Society of Automotive Engineers of Japan, Inc and The Japan Society of Mechanical Engineers in 2003

(4) Non-patent document 4: an article written by Akiba in "Engine Technology" vol. 5, No. 3, pages 36-42 co-edited by Automotive Engineers of Japan, Inc and The Japan Society of Mechanical Engineers in 2003

(5) Non-patent document 5: an article written by A. Chambers et al. in "The Journal of Physical Chemistry B" (U.S.A), vol. 102, pages 4253-4256, published by The American Chemical Society in 1998

(6) Non-patent document 6: an article written by Renzhi Ma et al. in "Journal of the American Chemical Society" (U.S.A), vol. 124, pages 7672-7673, published by The American Chemical Society in 2002

(7) Non-patent document 7: an article written by Nathaniel L. Rosi et al. in "Science" (U.S.A), vol. 300, pages 1127-1129, published by American Association for the Advancement of Science.

BRIEF SUMMARY OF THE INVENTION

The present invention has an object to provide a porous substance with a highly developed pore structure and in particular excellent gas absorbability and a process for producing such a substance as well as a process capable of producing a porous substance in a large scale.

As a result of an extensive study and research carried out the inventors of the present invention in order to solve the above-described problems, the present invention was accomplished on the basis of the finding that the above object was able to be achieved with a porous substance produced by dehydrogenating a compound having two or more, preferably three or more amine-borane adduct structures per molecule to be polymerized.

That is, the present invention relates to a process for producing a porous substance by dehydrogenating a compound having two or more, preferably three or more amine-borane adduct structures per molecule to be polymerized.

The present invention also relates to the foregoing process for producing a porous substance, wherein the amine-borane adduct compound is a compound having two or more amine-borane adduct structures in the skeleton of an organic compound.

The present invention also relates to the foregoing process wherein the amine-borane adduct structure is represented by formula (1) or (2) below:

$$—NHR^1.BHR^2R^3 \quad (1)$$

$$—NHR^1.BH=R^4 \quad (2)$$

wherein $R^1$, $R^2$, and $R^3$ are each independently hydrogen or a hydrocarbon group having 1 to 10 carbon atoms, and $R^4$ is a hydrocarbon group having 4 to 15 carbon atoms, both ends of which hydrocarbon group bond to boron atoms.

The present invention also relates to a porous substance produced by the above processes.

The present invention also relates to the porous substance used for gas absorption.

The present invention also relates to a method of absorbing gas using the porous substance.

DETAILED DESCRIPTION OF THE INVENTION

Figure 1:
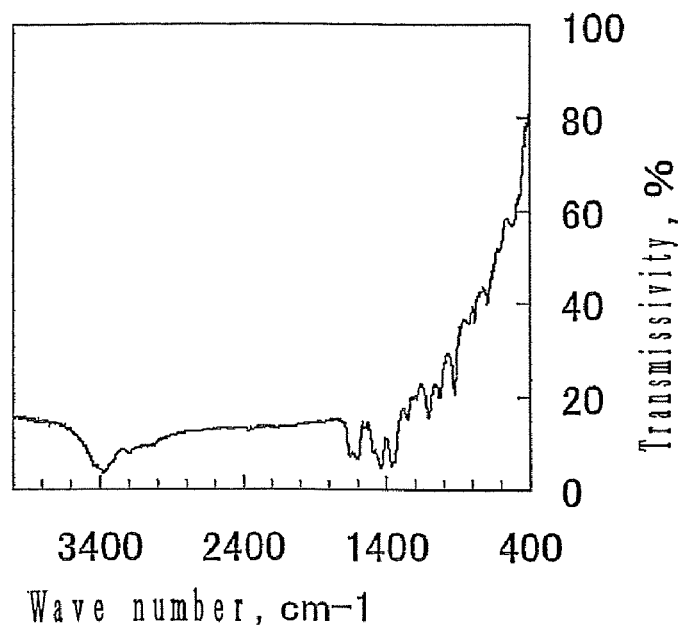
FIG. 1 is the infrared absorption spectrum of the porous substance produced in Example 1.

The present invention will be described in more detail below.

Amine-borane adduct compounds used in the present invention as the material of the porous substance are compounds having two or more, preferably three or more amine-borane adduct structures per molecule. In particular, the compounds are preferably those having two or more, preferably three or more amine-borane adduct structures per molecule in the skeleton of an organic compound and more preferably those having two or more, preferably three or more amine-borane adduct structures per molecule in a skeleton composed of an aromatic.

The most simple compound among amine-borane adduct compounds is the following compound comprising ammonia and borane:

$$NH_3.BH_3.$$

This compound is a type of complex compound wherein the unpaired electrons above the nitrogen atom of ammonia interact with the unoccupied orbital of borane. In the above formula, "." indicates such a complex bond, but in general the compound can stably exist at ambient temperatures.

The amine-borane adduct structure in the present invention refers to a structure represented by formula (3) below or a structure wherein any of hydrogen, preferably hydrogen on nitrogen in formula (3) is substituted by a hydrocarbon group:

$$—NH_2.BH_3 \quad (3).$$

Examples of a structure of formula (3) wherein any of hydrogen is substituted by a hydrocarbon group include those represented by formula (1) or (2):

$$—NHR^1.BHR^2R^3 \quad (1)$$

$$—NHR^1.BH=R^4 \quad (2)$$

wherein $R^1$, $R^2$ and $R^3$ are each independently hydrogen or a hydrocarbon group having 1 to 10 carbon atoms, and $R^4$ is a hydrocarbon group having 4 to 15 carbon atoms, both ends of which bond to boron atoms.

Specific examples of the amine-borane adduct structure include $—NH_2.BH_3$, $—NH(CH_3).BH_3$, $—NH(C_2H_5).BH_3$, $—NH(C_3H_7).BH_3$, $—NH(C_6H_5).BH_3$, $—NH_2.BH_2(CH_3)$, $—NH_2.BH_2(C_2H_5)$, $—NH_2.BH_2(C_3H_7)$, $—NH_2.BH_2(C_6H_5)$, $—NH_2.BH(CH_3)_2$, $—NH_2 BH(C_2H_5)_2$, $—NH_2.BH(C_3H_7)_2$, $—NH_2.BH(C_6H_5)_2$, $—NH_2.BH(—C_4H_8—)$, and $—NH_2.BH(—C_5H_{10}—)$. Most preferred is $—NH_2.BH_3$.

Examples of compounds having two or more amine-borane adduct structures per molecule include those having structures represented by formula (4):

$$\text{Skeleton–(amine-borane adduct structure)}_n \quad (4)$$

wherein n is an integer of 2 or greater.

The skeleton in formula (4) denotes the skeleton of a compound to which two or more amine-borane adduct structures can be bonded and is generally the skeleton of a compound containing at least two or more hydrogen atoms. Amine-borane adduct structures are bonded to the skeleton by substitution for the hydrogen atoms. More specific examples of the skeleton include organic or inorganic compound skeletons and complex skeletons such as metal complex skeletons of organic compounds and inorganic compounds. Preferred are organic compound skeletons, and more preferred are aromatic compound skeletons.

Specific examples of organic compound skeleton are given below, but amine-borane adduct structures may be substituted for any hydrogen in the organic compounds which are the bases of the skeletons. A part of hydrogen of the exemplified skeletons may be substituted by methyl or phenyl.

Preferred examples of the skeletons of organic compounds include skeletons of straight-chain hydrocarbons such as methane, ethane, propane and butane, those of branched hydrocarbons such as isobutane, isopentane and neopentane; those of alicyclics such as cyclopropane, cyclobutane, cyclopentane, cyclohexane, cycloheptane, cyclooctane, methylcyclohexane, dimethylcyclohexane and decalin; those of saturated heterocycles such as oxetane, tetrahydrofuran, dioxolane, dioxane, dioxane, pyrrolidine, piperidine, piperazine and morpholine; those of aromatics such as benzene, toluene, xylene, naphthalene, methylnaphthalene, dimethylnaphthalene, phenanthrene, tetralin, anthracene, pyrene and triphenylene; and those of heteroaromatics such as furan, thiophene, pyrrole, imidazole, triazole, oxazole, pyridine, pyrimidine, pyrazine, triazine, benzofuran, indole, quinoline and isoquinoline. More preferred are skeletons of aromatics and heteroaromatics.

Amine-borane adduct compounds having two or more amine-borane adduct structures per molecule used in the present invention may be those wherein the whole or a part of the amine-borane adduct structures may be the same or all of the structures may be different from each other.

Specific examples of amine-borane adduct compounds having two amine-borane adduct structures include:
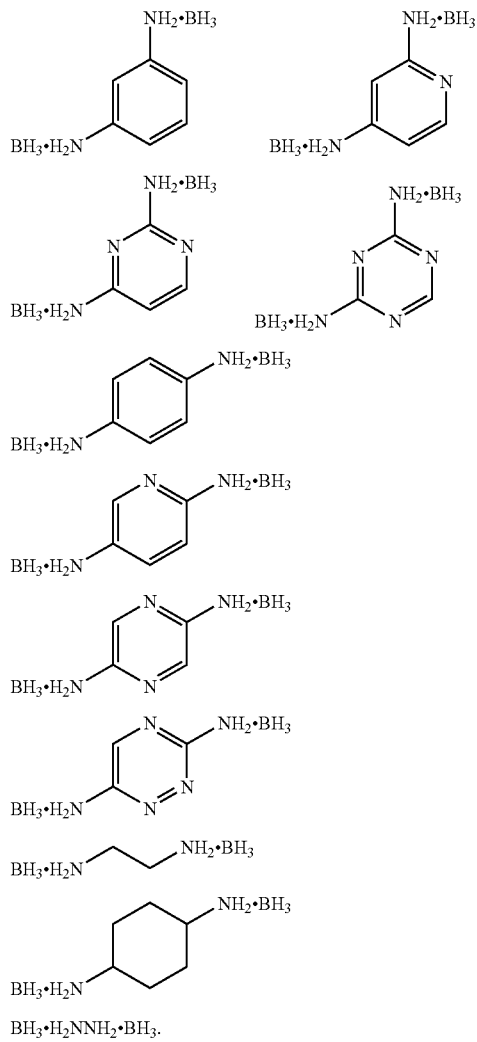
BH$_3$·H$_2$NNH$_2$·BH$_3$.
Specific examples of amine-borane adduct compounds having three or more amine-borane adduct structures include:
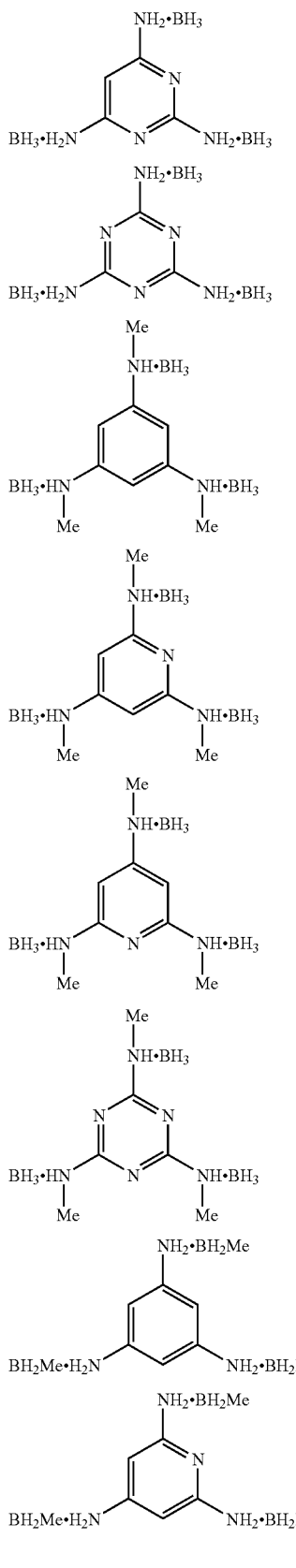

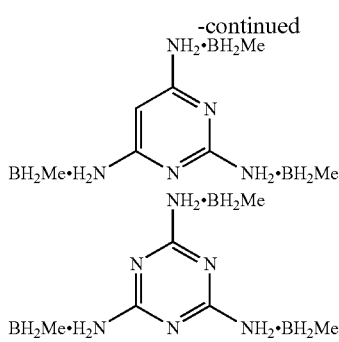

In the present invention, amine-borane adduct compounds may be used alone or in the form of a mixture. For example, the mixture may be a mixture of compounds having the same or different number of amine-borane adduct structure per molecule. Alternatively, the mixture may be further mixed with a compound having one amine-borane adduct structure such as $CH_3NH_2 \cdot BH_3$ or $C_6H_5NH_2 \cdot BH_3$ per molecule. In this case, the ratio of such an amine-borane adduct having one amine-borane adduct structure per molecule in the amine-borane adduct compound to be reacted is preferably 50 percent by mole or less, more preferably 40 percent by mole or less, and more preferably 30 percent by mole or less.

There is no particular restriction on the process of producing the amine-borane adduct compound having two or more amine-borane adduct structures per molecule used in the present invention. Generally, the amine-borane adduct compound may be produced by allowing a compound having two or more amino groups per molecule (hereinafter referred to as amine compound) to react with a borane compound such as diborane, a borane tetrahydrofuran complex, a borane dimethylsulfide complex, a borne triethylamine complex, or methylborane. Alternatively, the amine-borane adduct compound may be produced using a salt such as amine hydrochloride or amine sulfate as the amine compound and sodium borohydride or lithium borohydride as the borane compound.

The amine-borane adduct compound may be produced by reacting the amine compound or salt thereof with the borane compound in the equal weight of the amino group. Alternatively, the amine-borane adduct compound may be produced by reacting a compound having two or more borane groups per molecule and an organic compound having one or more amino group per molecule.

In general, the material ratio is determined so that the total number of the boron atom contained in the borane compound is substantially equal to the total number of the amino group contained in the amino compound and is defined as the basic quantity. However, either one of the total number of the boron atom or the total number of the amino group may be greater than the other. When the total number of the boron atom is greater, it is adjusted within a range of twice or less, preferably 1.5 time or less of the basic quantity of the total number of the amino group. When the total number of the amino group is greater, it is adjusted within a range of 1.5 time or less, preferably 1.2 time or less of the basic quantity.

Examples of amine compounds which may be used in the present invention include organic compounds having two or more amino groups per molecule. Specific examples include hydrazine, ethylenediamine, propylenediamine, phenylenediamine, diaminopyridine, diaminopyridazine, diaminopyrimidine, diaminopyrazine, triaminobenzene, triaminopyridine, triaminopyrimidine, melamine, tetraminobenzen, triaminonaphthalene, and tetraminonaphthalene. Particularly preferred are 1,3,5-triaminobenzene, 2,4,6-triaminopyrimidine and melamine.

When a compound having one amine-borane adduct structure per molecule is added, it may be a compound having one amino group per molecule, such as aniline, aminopyridine, aminopyridazine, aminopyrimidine, and aminopyrazine.

Next, dehydrogenation will be described.

In the present invention, a porous substance is produced by dehydrogenating the above-described amine-borane adduct compound to be polymerized. The dehydrogenation is accompanied with cross-linking polymerization and thus the reaction product will be a crosslinked polymer.

Any conventional method may be employed for dehydrogenation of an amine-borane adduct compound. For example, dehydrogenation may be carried out by heating the above-described amine-borane adduct compound. Thereupon, the reaction temperature is usually from room temperature to 400° C., preferably from 50 to 300° C., more preferably from 100 to 250° C.

The dehydrogenation reaction in the present invention may be carried out in the absence of a catalyst but may be carried out in the presence of a catalyst. The catalyst may be a homogeneous catalyst or a heterogeneous catalyst. Examples of the homogeneous catalyst include group VIII metals in the periodic table such as iron, cobalt, nickel, rhodium, ruthenium and iridium and complexes thereof. Examples of the heterogeneous catalyst include metal oxides such as zeolite, alumina, silica, silica-alumina, titania, magnesia, and calcia and catalysts wherein any of these metal oxide supports the foregoing metals or complexes thereof.

The dehydrogenation may be carried out in the absence of a solvent, but may be carried out in the presence of any suitable solvent (for example, tetrahydrofuran, toluene and 1-methyl-2-pyrrolidone).

Further, the dehydrogenation may be carried out under any pressurized condition such as atmospheric pressure, reduced pressure or pressurized condition and under an inert gas atmosphere such as of nitrogen or argon or a hydrogen atmosphere.

After the dehydrogenation, the volatile components such as the solvent is removed, followed by calcination at high temperatures. There is no particular restriction on the calcination temperature. However, the calcination is carried out at a temperature of usually 200 to 1000° C., preferably 300 to 800° C. The calcination is also preferably carried out under an inert gas atmosphere of nitrogen or argon or a hydrogen atmosphere.

The above-described process can produce a porous substance with highly developed pore structure. The BET surface area of the porous substance is usually 1 $m^2/g$ or greater, preferably 5 $m^2/g$ or greater, more preferably 10 $m^2/s$ or greater.

The porous substance is a lightweight material because it is composed of a material comprising lightweight elements such as boron, nitrogen, carbon, and hydrogen.

Therefore, the porous substance can be used as a catalyst, a catalyst support, an adsorbent, or a gas-absorbing material and in particular are suitable for storage and transportation of hydrogen or methane that is light and high in volume energy density.

A porous substance which is light and has a highly developed pore structure and excellent gas absorbability can be produced with a simple method in which to allow an amine-borane adduct compound that can be synthesized from a borane compound and an amine compound, which are industrially available with ease, to be dehydrogenated.

Hereinafter, the present invention will be described in more details by way of the following examples, which should not be construed as limiting the scope of the invention.

EXAMPLE 1

(1) Synthesis of 1,3,5-triaminobenezen-borane Adduct 2.46 g of 1,3,5-triaminobenzene were mixed with 200 mL of tetrahydrofuran (dehydration) and heated to a temperature of 80° C. under a nitrogen flow to be dissolved. To the resulting solution while being cooled in an ice bath were added gradually dropwise 60 mL of 1.0 M borane tetrahydrofuran complex. After the mixture was stirred at room temperature for one hour, it was vacuum-dried, cooled in a dry ice/acetone bath, thereby obtaining 3.2 g of 1,3,5-triaminobenzene-borane adduct in the form of brownish residual.

(2) Production of a Porous Substance

Dehydrogenation was carried out by heating 500 mg of the resulting 1,3,5-triaminobenzene-borane adduct at a temperature of 100° C. under a nitrogen atmosphere. After foaming was over, vacuum-evacuation was carried out at a temperature of 100° C.

FIG. 1 shows the infrared absorption spectrum of the resulting porous substance. As the result of analysis of the spectrum, it was confirmed that peaks originating from the BN expansion and contraction emerged at 1373 cm$^{-1}$ and 1471 cm$^{-1}$.

(3) Measurement of Hydrogen Absorbability

The hydrogen absorbability of the porous substance was evaluated by a volumetric analysis. Before the evaluation, the porous substance was treated in vacuo at a temperature of 100° C. for two hours. After the pressure was increased to 9.5 MPa at room temperature to measure the hydrogen absorbability, the substance absorbed 0.22 percent by mass of hydrogen.

EXAMPLE 2

The porous substance produced in Example 1 was calcined at a temperature of 600° C. under a nitrogen flow for two hours. As the result of measurement of the BET surface area of the calcined product by a nitrogen adsorption method, it was confirmed that the BET surface area was 23 m$^2$/g.

Thereafter, the hydrogen absorbability of the calcined product was evaluated by a volumetric analysis. Before the evaluation, the porous substance was treated in vacuo at a temperature of 100° C. for two hours. After the pressure was increased to 9.5 MPa at room temperature to measure the hydrogen absorbability, the substance absorbed 0.35 percent by mass of hydrogen.

EXAMPLE 3

(1) Synthesis of 2,4,6-triaminopyrimidine-borane Adduct 0.6 g of 2,4,6-triaminopyrimidine was mixed with 200 mL of 1-methyl-2-pyrrolidone (dehydration) and heated to a temperature of 80° C. under a nitrogen flow to be dissolved. To the resulting solution while being cooled in an ice bath were added gradually dropwise 30 mL of 1.0 M borane tetrahydrofuran complex. After the mixture was stirred at room temperature for one hour, followed by heating to a temperature of 60° C. and then stirring for two hours, a large amount of precipitate was produced. The reaction solution was subjected to suction filtration to collect the precipitate, which was then vacuum-dried at a temperature of 60° C. for 8 hours thereby obtaining 0.7 g of 2,4,6-triaminopyrimidine-borane adduct in the form of brownish residue.

(2) Production of a Porous Substance

Dehydrogenation was carried out by heating 500 mg of the resulting 2,4,6-triaminopyrimidine adduct at a temperature of 100° C. in vacuo for 8 hours.

Figure 2:
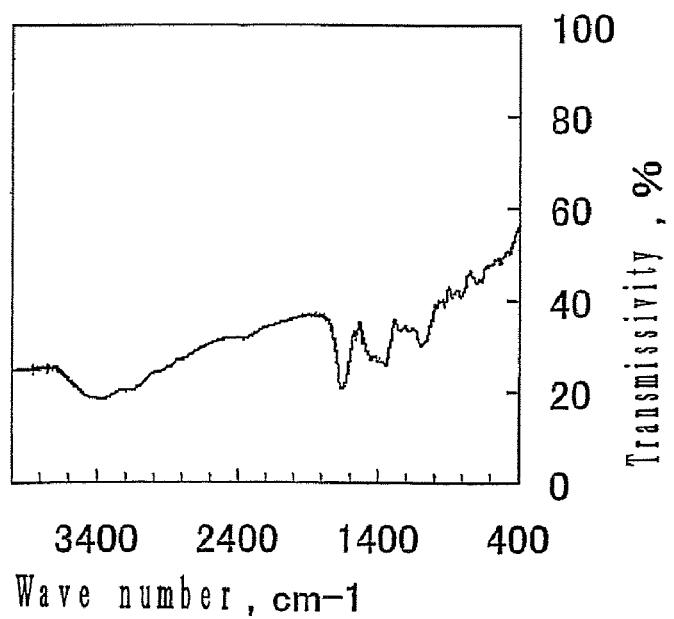
FIG. 2 is the infrared absorption spectrum of the porous substance produced in Example 3.

FIG. 2 shows the infrared absorption spectrum of the resulting porous substance. As the result of analysis of the spectrum, it was confirmed that a peak originating from the BN expansion and contraction emerged at 1384 cm$^{-1}$.

(3) Measurement of Hydrogen Absorbability

The hydrogen absorbability of the porous substance was evaluated by a volumetric analysis. Before the evaluation, the porous substance was treated in vacuo at a temperature of 100° C. for two hours. After the pressure was increased to 9.5 MPa at room temperature to measure the hydrogen absorbability, the substance absorbed 0.2 percent by mass of hydrogen.

EXAMPLE 4

The porous substance produced in Example 3 was calcined at a temperature of 600° C. under a nitrogen flow for two hours. As the result of measurement of the BET surface area of the calcined product by a nitrogen adsorption method, it was confirmed that the BET surface area was 13 m$^2$/g.

Thereafter, the hydrogen absorbability of the calcined product was evaluated by a volumetric analysis. Before the evaluation, the porous substance was treated in vacuo at a temperature of 100° C. for two hours. After the pressure was increased to 9.5 MPa at room temperature to measure the hydrogen absorbability, the substance absorbed 0.24 percent by mass of hydrogen.

EXAMPLE 5

(1) Synthesis of 1,4-phenylenediamine-borane Adduct 2.16 g of 1,4-phenylenediamine was mixed with 200 mL of tetrahydrofuran (dehydration) to be dissolved. To the resulting solution while being cooled in an ice bath were added gradually dropwise 40 mL of 1.0 M borane tetrahydrofuran complex. After the mixture was stirred at room temperature for one hour, it was vacuum-dried, while being cooled in a dry ice/acetone bath, thereby obtaining 2.7 g of 1,4-phenylenediamine-borane adduct in the form of colorless residual.

(2) Production of a Porous Substance

Dehydrogenation was carried out by heating 500 mg of the resulting 1,4-phenylenediamine-borane adduct at a temperature of 100° C. under a nitrogen atmosphere. After foaming was over, vacuum-evacuation was carried out at a temperature of 100° C.

As the result of analysis of the infrared absorption spectrum of the resulting porous substance, it was confirmed that peaks originating from the BN expansion and contraction emerged at 1375 cm$^{-1}$ and 1473 cm$^{-1}$.

(3) Measurement of Hydrogen Absorbability

The hydrogen absorbability of the porous substance was evaluated by a volumetric analysis. Before the evaluation, the porous substance was treated in vacuo at a temperature of 100° C. for two hours. After the pressure was increased to 9.5 MPa at room temperature to measure the hydrogen absorbability, the substance absorbed 0.1 percent by mass of hydrogen.

EXAMPLE 6

The porous substance produced in Example 5 was calcined at a temperature of 600° C. under a nitrogen flow for two hours. As the result of measurement of the BET surface area of the calcined product by a nitrogen adsorption method, it was confirmed that the BET surface area was 18 m$^2$/g.

Thereafter, the hydrogen absorbability of the calcined product was evaluated by a volumetric analysis. Before the evaluation, the porous substance was treated in vacuo at a temperature of 100° C. for two hours. After the pressure was increased to 9.5 MPa at room temperature to measure the hydrogen absorbability, the substance absorbed 0.27 percent by mass of hydrogen.

EXAMPLE 7

2.18 g of 2,6-diaminopyridine was dissolved in 200 mL of 1-methyl-2-pyrrolidone (dehydration). To the resulting solution while being cooled in an ice bath were added gradually dropwise 40 mL of 1.0 M borane tetrahydrofuran complex.

The resulting 2,6-diaminopyridine-borane adduct solution was dehydrogenated, while being heated in vacuo at a temperature of 100° C. to remove the solvent over 8 hours.

As the result of analysis of the infrared absorption spectrum of the resulting porous substance, it was confirmed that a peak originating from the BN expansion and contraction emerged at 1387 cm$^{-1}$.

The hydrogen absorbability of the porous substance was evaluated by a volumetric analysis. Before the evaluation, the porous substance was treated in vacuo at a temperature of 100° C. for two hours. After the pressure was increased to 9.5 MPa at room temperature to measure the hydrogen absorbability, the substance absorbed 0.15 percent by mass of hydrogen.

EXAMPLE 8

The porous substance produced in Example 7 was calcined at a temperature of 600° C. under a nitrogen flow for two hours. As the result of measurement of the BET surface area of the calcined product by a nitrogen adsorption method, it was confirmed that the BET surface area was 10 m$^2$/g.

Thereafter, the hydrogen absorbability of the calcined product was evaluated by a volumetric analysis. Before the evaluation, the porous substance was treated in vacuo at a temperature of 100° C. for two hours. After the pressure was increased to 9.5 MPa at room temperature to measure the hydrogen absorbability, the substance absorbed 0.2 percent by mass of hydrogen.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process for producing a porous substance for absorbing hydrogen comprising dehydrogenating an aromatic compound having two or more amine-borane adduct structures per molecule to polymerize the compound, wherein the aromatic compound comprises substituent groups represented by formula (1) or (2) below as the amine-borane structures:

$$—NHR^1 \cdot BHR^2R^3 \quad (1)$$

$$—NHR^1 \cdot BH{=\!\!=}R^4 \quad (2)$$

wherein $R^1$, $R^2$, and $R^3$ are each independently hydrogen or a hydrocarbon group having 1 to 10 carbon atoms, and $R^4$ is a hydrocarbon group having 4 to 15 carbon atoms, both ends of which hydrocarbon group bond to boron atoms.

2. A porous substance produced by the process according to claim 1.

3. A method of absorbing gas, wherein it uses the porous substance according to claim 2.

4. The process for producing a porous substance according to claim 1, wherein the compound has two or three amine-borane adduct structures.

5. The process for producing a porous substance according to claim 1, wherein the compound has a substituent group represented by formula (1) below as the amine-borane structure:

$$—NHR^1 \cdot BHR^2R^3 \quad (1)$$

wherein $R^1$, $R^2$, and $R^3$ are each independently hydrogen or a hydrocarbon group having 1 to 10 carbon atoms.

6. The process for producing a porous substance according to claim 5, wherein $R^1$, $R^2$, and $R^3$ in formula (1) are each independently hydrogen or a hydrocarbon group having 1 to 6 carbon atoms.

7. The process for producing a porous substance according to claim 5, wherein $R^1$, $R^2$, and $R^3$ in formula (1) are each independently hydrogen or a methyl group.

8. The process for producing a porous substance according to claim 1, wherein the aromatic compound is selected from the group consisting of benzene, pyridine, pyrimidine, pyrazine and triazine.

* * * * *